(12) United States Patent
Roeder

(10) Patent No.: US 9,220,614 B2
(45) Date of Patent: Dec. 29, 2015

(54) ENDOVASCULAR GRAFTS FOR TREATING THE ILIAC ARTERIES AND METHODS OF DELIVERY AND DEPLOYMENT THEREOF

(71) Applicant: COOK MEDICAL TECHNOLOGIES LLC, Bloomington, IN (US)

(72) Inventor: Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/793,878

(22) Filed: Mar. 11, 2013

(65) Prior Publication Data

US 2014/0257464 A1 Sep. 11, 2014

(51) Int. Cl.
*A61F 2/07* (2013.01)
*A61F 2/856* (2013.01)
*A61F 2/954* (2013.01)
*A61F 2/966* (2013.01)
*A61F 2/06* (2013.01)

(52) U.S. Cl.
CPC . *A61F 2/856* (2013.01); *A61F 2/07* (2013.01); *A61F 2/954* (2013.01); *A61F 2/966* (2013.01); *A61F 2002/061* (2013.01); *A61F 2002/067* (2013.01)

(58) Field of Classification Search
CPC ..... A61F 2/07; A61F 2/856; A61F 2002/061; A61F 2002/065; A61F 2002/067

USPC ........................................ 623/1.13, 1.27, 1.35
See application file for complete search history.

(56) References Cited

U.S. PATENT DOCUMENTS

| | | | |
|---|---|---|---|
| 7,105,020 B2 | 9/2006 | Greenberg et al. | |
| 7,407,509 B2 | 8/2008 | Greenberg et al. | |
| 8,012,193 B2 | 9/2011 | Hartley et al. | |
| 2007/0250154 A1* | 10/2007 | Greenberg et al. | 623/1.13 |
| 2009/0125100 A1* | 5/2009 | Mead | 623/1.35 |

FOREIGN PATENT DOCUMENTS

| | | |
|---|---|---|
| AU | 2012258394 B1 | 3/2013 |
| EP | 2 110 102 A1 | 10/2009 |
| WO | WO 2009/046372 A2 | 4/2009 |

OTHER PUBLICATIONS

Extended European Search Report for EP 14275022 dated May 28, 2014 (7 pages).

* cited by examiner

*Primary Examiner* — Dinah Baria
(74) *Attorney, Agent, or Firm* — Brinks Gilson & Lione

(57) ABSTRACT

This invention relates generally to medical devices, and more particularly, to endovascular grafts and methods for treating branched vessels in diverse patient populations including those with shorter than average common iliac arteries. A bifurcated stent graft as described herein comprises adjacent facing fenestrations formed in the graft legs in order to permit proper placement of an "up-and-over sheath" and a side branch which may be proximally located in order to properly align the side branch with the opening of the branch vessel such as the internal iliac artery while keeping the graft bifurcation seated near the aortic bifurcation.

17 Claims, 13 Drawing Sheets

ENDOVASCULAR GRAFTS FOR TREATING THE ILIAC ARTERIES AND METHODS OF DELIVERY AND DEPLOYMENT THEREOF

BACKGROUND

This invention relates generally to medical devices, and more particularly, to endovascular stent grafts and methods for treating branched vessels.

Stent grafts may be inserted into an anatomical vessel or duct for various purposes. For example, stent grafts are used for treatment of vasculature in the human or animal body to bypass a repair or defect in the vasculature or to maintain or restore patency in a formerly blocked or constricted passageway. For example, a stent graft may extend proximally and/or distally away from a vascular defect, including a diseased portion of an aneurysm, and engage a healthy portion of a vessel wall.

In many cases, a damaged or defective portion of the vasculature may include a branched or side vessel. More particularly, endovascular treatment of aortoiliac and internal iliac aneurysms is increasing in frequency in diverse patient populations. Fenestrated devices such as branched stent grafts having a side arm extending towards the internal iliac artery are known for treating such branched vessels. However, the anatomy of the vasculature may be unique from one patient population to the next and also among individual patients. In one example, branched stent grafts have been used to treat patients having common iliac arteries of a certain average length, such as approximately 40 mm in length or greater. However, the length of the common iliac arteries among certain patient populations, especially patients of Asian descent, may be on average shorter, down to 20 mm in length or even less. As a result, precise placement of the fenestration in the branched graft, which permits placement of an "up-and-over sheath" from the contralateral femoral artery, through the ipsilateral leg to the ipsilateral internal iliac limits treatment to patients with longer common iliac arteries in order to keep the graft bifurcation near the aortic bifurcation. Further, to align the side arm of the branched graft with the orifice of the internal iliac artery may present a challenge in patients having a shorter than average anatomy.

In addition, access to and introduction of a stent graft into a branched vessel and successful deployment of a stent graft in such vessels may often depend upon a favorable layout of the arteries. One approach that has been investigated includes accessing the target location(s) within the branched vessels by a contralateral or crossover approach. In other words, a bifurcated aortic stent graft having a longer leg that extends into one common iliac artery and a shorter contralateral leg or stump extending into the other common iliac artery may first be placed. The location of the side branch extending from the longer leg of the bifurcated graft may be adjacent to the opening of the internal iliac artery depending on the particular anatomy of the patient being treated. An additional graft or extension may then be introduced into the contralateral femoral artery, over the aortic bifurcation, and through the side branch, for placement of the graft extension in the internal iliac artery.

Accordingly, in order to treat diverse patient populations including those with shorter than average iliac arteries, it may be desirable to provide a bifurcated stent graft in which the fenestration is located more proximally in order to permit proper placement of an "up-and-over sheath" and the side branch is located more proximally in order to properly align the side branch with the opening of the branched vessel (such as the internal iliac artery), all while keeping the bifurcation between the legs of the stent graft near the aortic bifurcation. While the apparatus and methods disclosed herein are generally in relation to a stent graft and method of delivery and deployment thereof into a common iliac artery where it is necessary to extend a side branch from a main portion or body of the graft into an internal iliac artery, it is also contemplated that the systems and methods are not so limited and may relate to any other target locations within a vessel lumen in which such a graft and deployment therein is necessary or desired.

SUMMARY

The present disclosure provides an endovascular stent graft and method for treating branched vessels including the iliac arteries.

In one example, the stent graft comprises a main tubular body of a biocompatible graft material having a proximal end portion and a distal end portion and a lumen extending between the proximal and distal end portions. A first leg defining a first lumen and a second leg defining a second lumen extend from the distal end portion of the main tubular body and the first and second lumens are in fluid communication with the lumen of the main tubular body. The first and second legs each have an internal surface and an external surface and the respective internal surfaces of the first and second legs are adjacent. The stent graft further preferably comprises a fenestration formed on the first and second adjacent internal surfaces which at least partially align with each other. The adjacent fenestrations may be attached. A side branch extends from at least one of the first and second legs. In one example, the side branch comprises a tubular body of a biocompatible graft material having a proximal end portion and a distal end portion and a lumen extending between the proximal and distal end portions. The side branch lumen is in fluid communication with the lumen of the at least one of the first and second legs from which it extends. The proximal end portion of the side branch extends from the at least one of the first and second legs at a location that is substantially adjacent to the fenestration formed in the internal surface of the leg. In one example, the stent graft is configured to be deployed into the vasculature of a patient with the main tubular body being located in the common iliac artery and the side branch being directed towards an internal iliac artery of the common iliac artery.

A method for treating a diseased vessel is described. The method comprises the steps of introducing a delivery device carrying an endovascular graft into a patient's vasculature. The endovascular graft comprises a main tubular body of a biocompatible graft material having a proximal end portion and a distal end portion, a long leg and a short leg each extending from the distal end portion of the main tubular body and wherein each of the legs has an internal surface and an external surface and wherein the respective internal surfaces of the legs are adjacent. The graft further comprises a first fenestration formed in each of the adjacent internal surfaces which at least partially align with each other, and which may be attached. A side branch comprising a tubular body of biocompatible graft material extends from the long leg, and has a proximal end portion and a distal end portion and a lumen extending therebetween. The proximal end portion of the side branch extends from the long leg at a location that is substantially adjacent to the first fenestration formed therein. The method further comprises positioning the endovascular graft in the patient's vasculature such that at least the long leg is located in the common iliac artery and the side branch is directed towards an internal iliac artery of the common iliac artery and at least partially deploying the endovascular graft in the patient's vasculature.

The method further comprises introducing a second delivery device though a lumen of the short leg. The second delivery device preferably carries a second endovascular graft thereon and wherein the second endovascular graft has a tubular body defining a lumen. The second delivery device is advanced through the respective first fenestrations formed in the adjacent internal surfaces of the long and short legs and into the lumen of the side branch. The method further comprises positioning the second endovascular graft within the internal iliac artery and at least partially deploying the second endovascular graft in the internal iliac artery.

DETAILED DESCRIPTION

Throughout this specification the terms proximal and proximally are used for a position or direction towards the patient's heart and the terms distal and distally are used for a position or direction away the patient's heart. The embodiments described below are in connection with the deployment of an implantable medical device, such as an endovascular prosthesis. It will be understood that the apparatus and methods can be used for deploying a range of implantable medical devices including stents, stent grafts, occlusion devices and the like.

Figure 1:
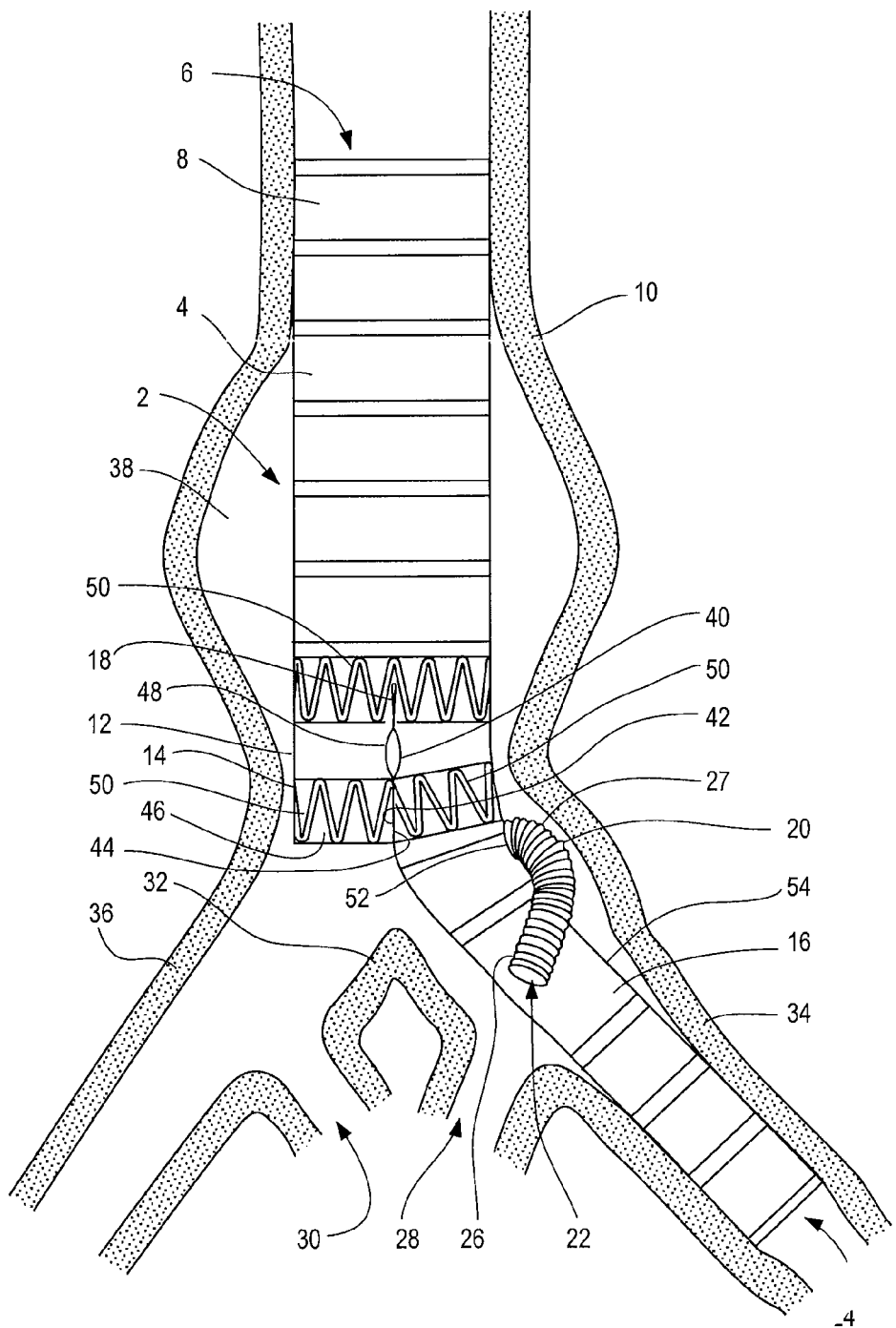
FIG. 1 shows one example of a bifurcated stent graft located in a patient's vasculature with a longer leg extending into an iliac artery and a side arm extending towards the opening of an internal iliac artery.

Referring now to FIG. 1, an exemplary bifurcated stent graft is shown generally at 2. The bifurcated graft 2 preferably includes a substantially tubular main graft body 4 defining a lumen 6. The proximal end portion 8 of the main graft body 4 is configured for engagement with a healthy portion of the aorta 10 just distal of the renal arteries and/or configured for attachment or connection to another graft. The distal end portion 12 of the main graft body 4 has a short contralateral leg or stump 14 and a long leg 16 extending from graft bifurcation 18.

A side branch 20, also preferably having a substantially tubular body defining a lumen 22, extends from the long leg 16 of the bifurcated graft 2 and may be integrally formed with the long leg 16, or alternatively, the side branch 20 may be a separately formed component that is secured to the long leg 16 such as by stitching, bonding, adhesive or the like. In either case, the lumen 22 of the side branch 20 is in fluid communication with the lumen 24 of the long leg 16. The side branch 20 extends in a distal direction and, in one example, helically partly around the longer leg 16 and has a distal end 26 remote from its point of connection or attachment with the longer leg 16, which distal end 26 preferably opens adjacent to the ipsilateral internal iliac artery 28. Each of the legs has a distal end portion. At least a portion of the proximal end of the side branch extends from the longer leg at a location that is proximal to the distal end portion of the shorter leg.

In one example, the bifurcated graft 2 and the side branch 20 are preferably constructed of one or more biocompatible materials including, but not limited to, polyesters, fluorinated polymers and polyurethanes and/or may be made from natural or organic materials. The materials may also be subjected to surface modifications or coatings. In a preferred example, as shown in FIG. 1, the bifurcated graft 2 is configured to be deployed into the vasculature of a patient with the main tubular body 4 being located in the descending aorta 10, which is shown in FIG. 1 as having aneurysm 38 (with the graft bifurcation 18 preferably seated proximal to the aortic bifurcation 32) while the longer leg 16 extends into the ipsilateral common iliac artery 34 and the contralateral stump 14 is directed towards the contralateral common iliac artery 36. The side branch 20 is directed towards the ipsilateral internal iliac artery 28 of the common iliac artery 34. However, other stent graft configurations for deployment into various other body vessels are also contemplated depending on various factors including, but not limited to the particular vessel(s) being treated and/or the location of a particular damaged or diseased portion of a vessel.

As illustrated in FIG. 1, the longer leg 16 includes an opening or fenestration 40. The fenestration 40 is preferably formed on an inside surface 42 of the leg 16, or in other words, formed in the surface 42 that faces and/or abuts the inside surface 44 of the contralateral stump 14. Preferably, the fenestration 40 is located just distal to the graft bifurcation 18 and proximal to a distal end 46 of the contralateral stump 14. In other words, the fenestration 40 formed in the longer leg 16 is preferably "sandwiched" between the longer 16 and shorter 14 legs of the bifurcated graft 2. In one example, the fenestration 40 may be an opening approximately 6 mm in diameter, although other sizes and shapes of the opening are also contemplated, such as any aperture and/or slit. In a one embodiment, the fenestration 40 may be open, but alternatively, it may also be self-sealing, such as by a flap of graft material, or by similar known self-sealing methods.

Similarly, the contralateral stump 14 also includes an opening or fenestration 48 formed on the inside surface 44 thereof. Like the fenestration 40 described above, fenestration 48 may be a variety of shapes or sizes. Fenestration 48 is preferably located just distal to the graft bifurcation 18 and proximal to a distal end 46 of the contralateral stump 14. As shown in FIG. 1, for example, it is preferable that the fenestration 48 formed in the contralateral stump 14 is located opposite from and is aligned, or at least partially aligned, with the fenestration 40 formed in the longer leg 16, and is also sandwiched between the longer 16 and shorter 14 legs of the bifurcated graft 2. As such, the respective openings or fenestrations 40 and 48 face or at least partially align with each other between the abutting inner surfaces 42, 44 of the longer 16 and shorter 14 legs, respectively. Preferably, the respective fenestrations 40 and 48 are connected so as to provide a flow path for fluid flow between the legs and/or for another device or object to be passed therethrough. In one non-limiting example, the attached fenestrations 40, 48 may be separated as necessary or desired during a particular procedure. Separation of the respective fenestrations may help facilitate the introduction of another delivery device and/or stent graft as it passes through the lumen of one leg, through the fenestrations 40, 48 and into the lumen of the other leg.

In one example, the attached fenestrations 40, 48 are open and in fluid flow communication with each other. Alternatively, one or both of the fenestrations 40, 48 may be separated such that one or both are open and remain open until an extension graft 94 (as described below and shown in FIG. 14) is introduced into the patient's vasculature and added onto the contralateral stump 14. In other words, once added onto the stump 14, a proximal end portion of the extension graft 94 can cover all or a portion of the contralateral stump 14, thus also covering, closing and/or sealing the fenestration 48 as will be described in further detail below. In addition, one or both of the fenestrations 40, 48, if desired, may be defined and/or reinforced by a ring of stitching, wires or other similar reinforcement materials or methods.

Preferably, a resilient self-expanding stent 50 may be located proximally, distally or, preferably, both proximally and distally of the fenestrations 40 and 48, respectively. The one or more stents 50 may provide reinforcement and flexibility of the longer 16 and shorter 14 legs near the facing, and preferably attached, fenestrations 40 and 48.

As FIG. 1 shows, the proximal end portion 27 of the side branch 20 is attached to or extends from the longer leg 16 at a location that is near or adjacent to the fenestration 40 formed in the longer leg 16. In one example, the side branch 20 may extend from an opening or fenestration 52 located and formed near an external surface 54 of the longer leg 16 that may be diametrically opposite to the fenestration 40 formed in the inner surface 42 of the longer leg 16 or, as shown in FIG. 1 the side branch 20 may extend from a location on the longer leg 16 that is near or substantially adjacent to the fenestration 40 formed in the inner surface 42 of the longer leg 16.

Figure 2:
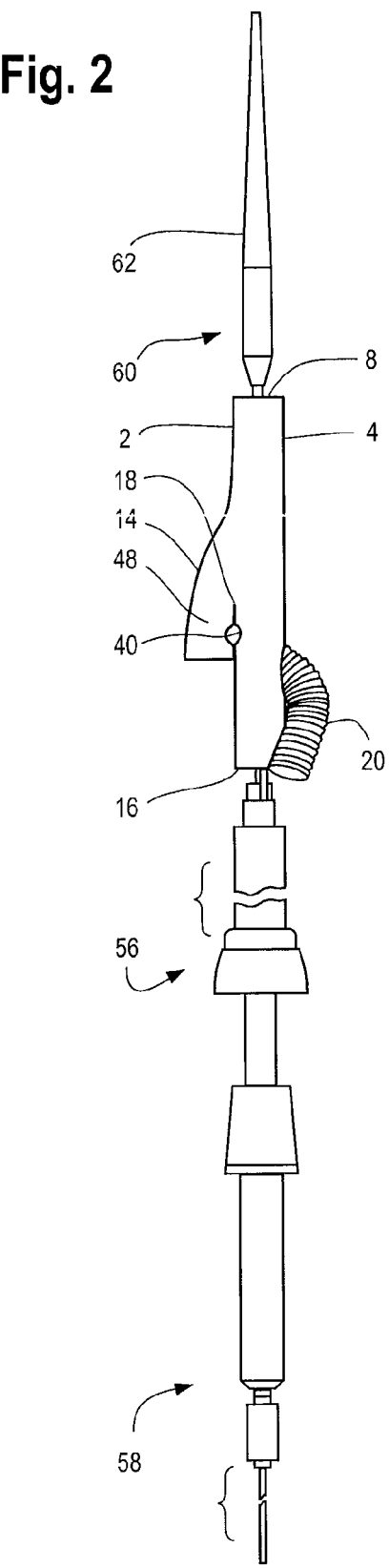
FIG. 2 is a side view of a bifurcated stent graft carried by the proximal end portion of a delivery device.

Referring now to FIG. 2, an example of a stent graft delivery device 56 is shown, which is useful in understanding the principles of the delivery and deployment methods described herein. The delivery device 56 includes a distal external manipulation section shown generally at 58 which is operated by a surgeon or clinician and a proximal end shown generally at 60 which is introduced intraluminally into a patient. During the medical procedure to deploy the stent graft 2, the proximal end 60 will travel through the vessel lumen to a desired deployment site. The external manipulation section 58, which is acted upon by a user to manipulate the device 56, remains outside of the patient throughout the procedure.

The delivery device 56 has a nose cone dilator 62 at its proximal end 60 and a stent graft 2 according to one example of the present invention is mounted onto the device 56. In the "pre-deployment" condition, or prior to deployment of the stent graft 2 into the vasculature of a patient, the device 56 is preferably pre-loaded with various components thereon. As shown in FIG. 5, a delivery device 56 has been deployed over a guide wire 64 so that its nose cone 62 extends up into the aneurysm 38 and the distal end 66 of the nose cone 62 is substantially adjacent to the aortic bifurcation 32. The stent graft 2 is compressed by the sheath 68. However, for convenience, in FIGS. 2-4, the sheath 68 has been withdrawn to show the details of the pre-loaded graft 2 that lies underneath it.

Figure 3:
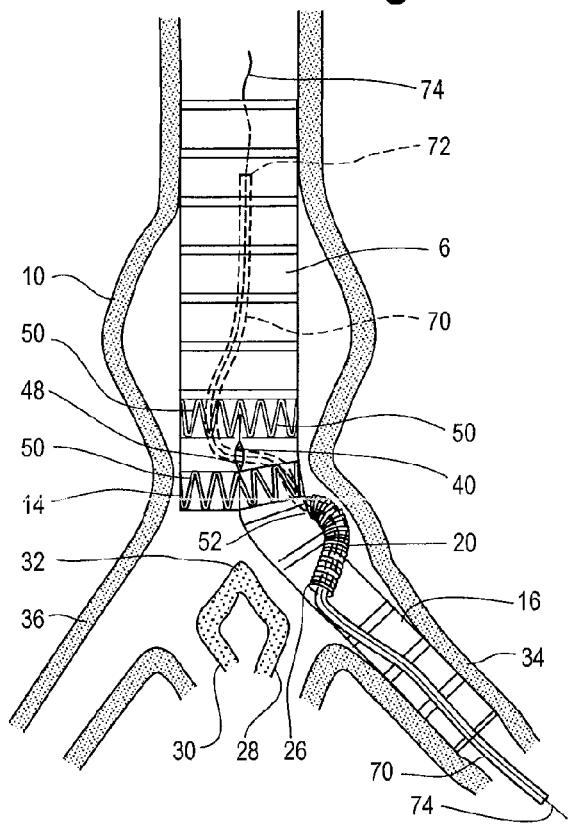
FIG. 3 illustrates one example of a bifurcated stent graft that is pre-loaded with a catheter and a guide wire running therethrough.
Figure 5:
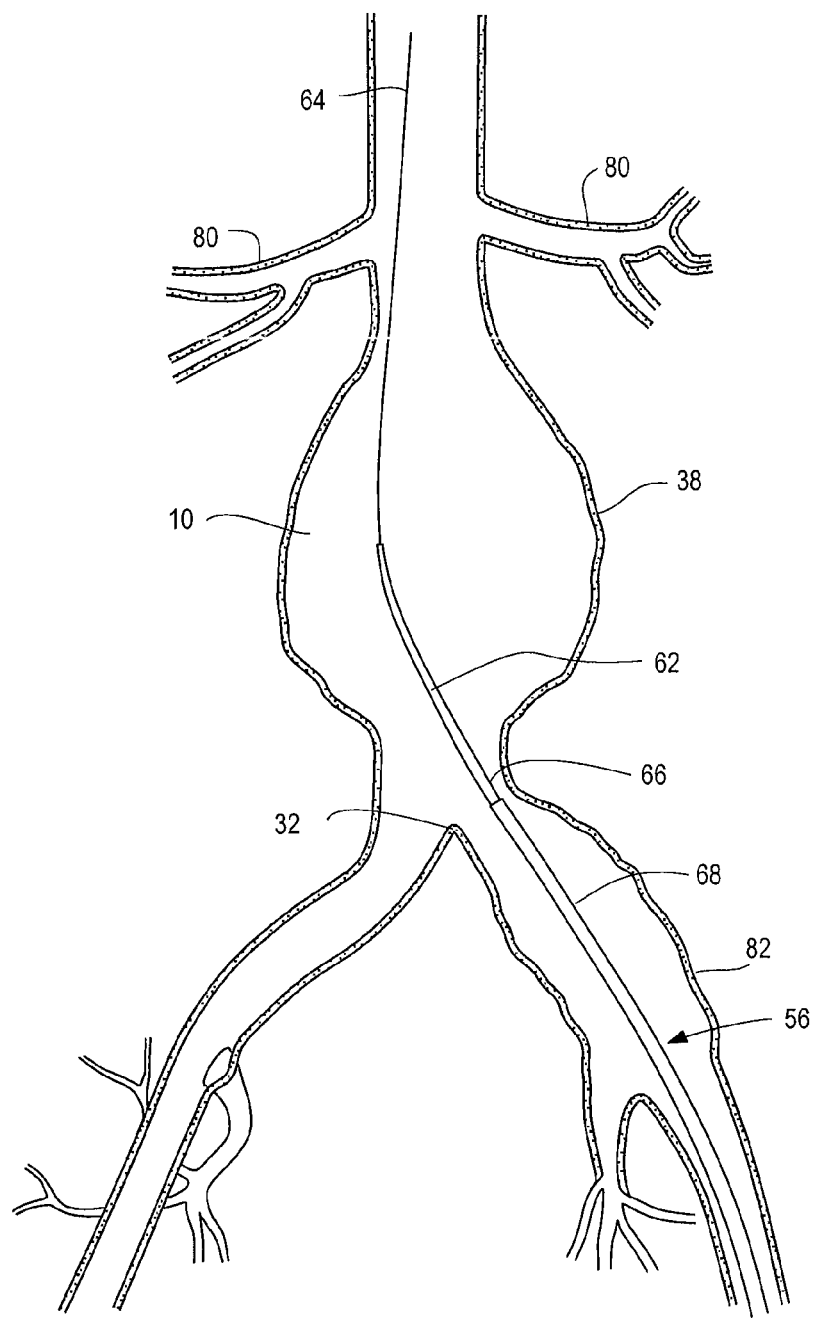
FIGS. 5-14 show a partial view of the vasculature of a patient and one example of the various stages of delivery and deployment of a stent graft therein.
Figure 6:
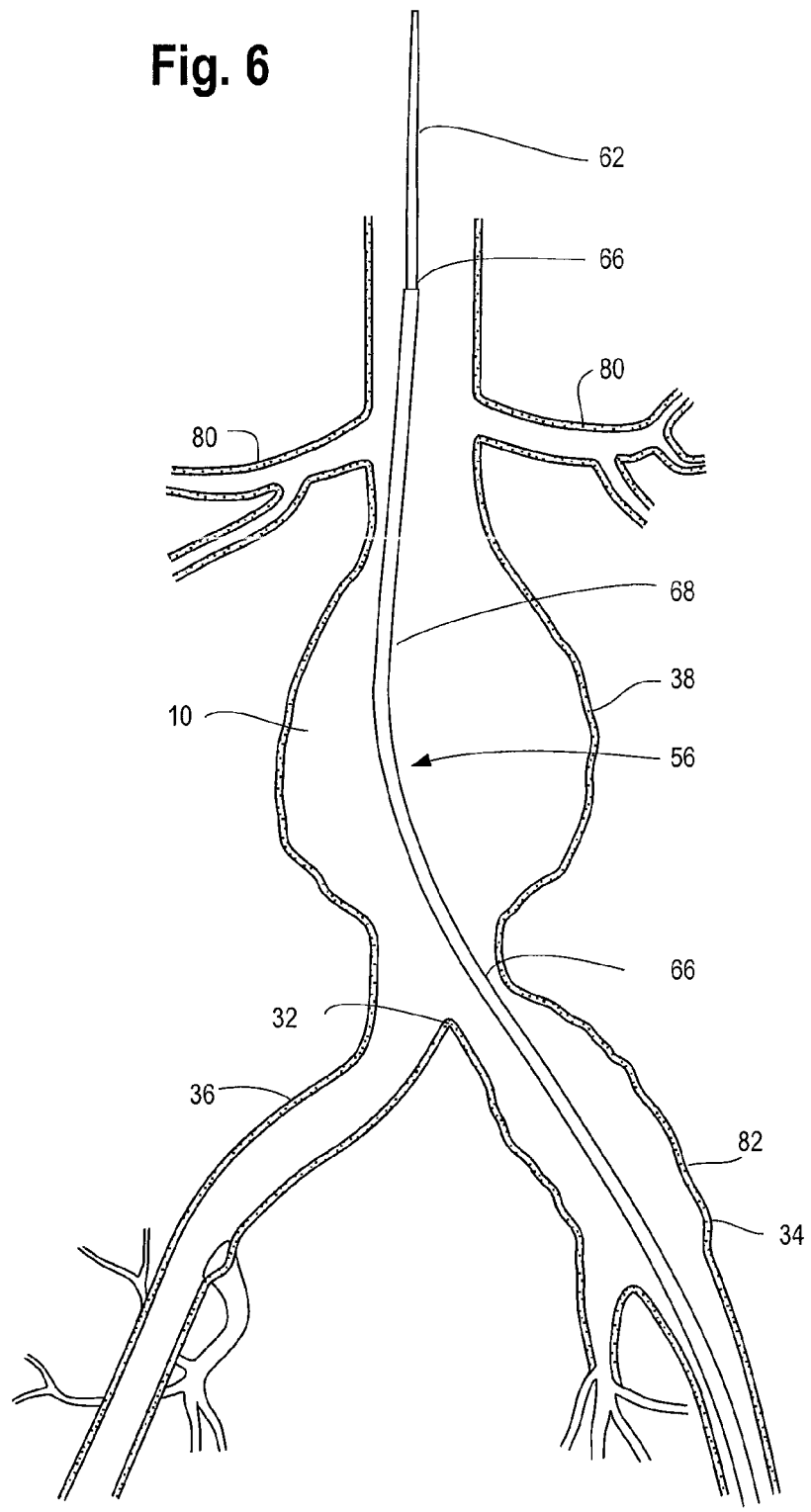

As shown in FIG. 3, the delivery device 56 with a stent graft 2 carried at the proximal end 62 thereof (which has been extended into the patient's vasculature as shown in FIGS. 5 and 6), may be pre-loaded with an in-dwelling catheter 70. The catheter 70 may extend from the distal external manipulation portion 58 of the delivery device, along the length of the device 56, through the distal end 26 of the side arm or branch 20, through the adjacent and attached fenestrations 40 and 48 and continue proximally up through the main graft lumen 6 such that the proximal tip 72 of the pre-loaded catheter 70 is positioned within the main graft lumen 6. The catheter 70 may include a guide wire 74 running therethrough. As will be described in further detail below, the guide wire 74 may be snared from the contralateral stump 14 inside of the main graft lumen 6 to create an "up and over pathway" or "through wire", or, in other words, a wire or pathway that preferably runs from one groin to the other groin. The pathway provided by the through wire may be used to ultimately facilitate the introduction and placement of a delivery device and stent graft in a desired location within the lumen of a branched vessel (such as in an internal iliac artery), by providing a pathway over which the delivery device may be tracked or extended, as will be described in further detail below.

Figure 4:
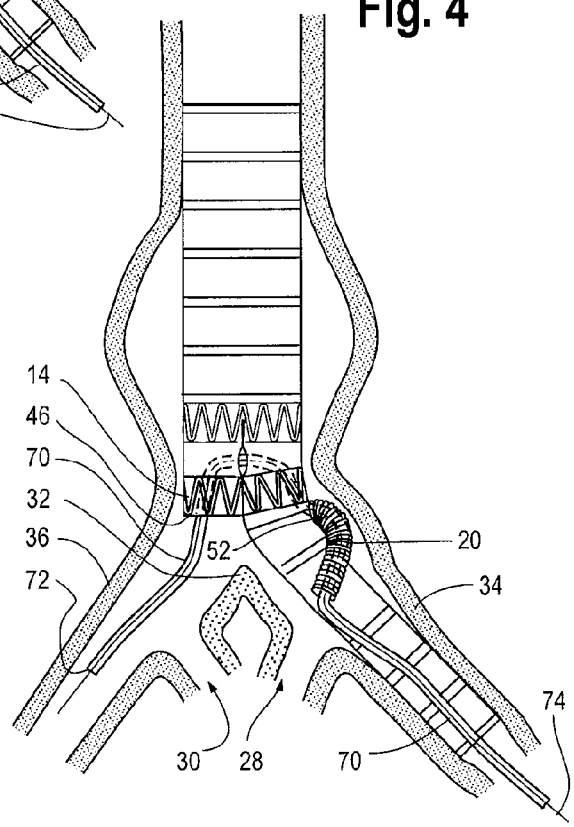
FIG. 4 illustrates another example of a bifurcated stent graft that is pre-loaded with a catheter and a guide wire running therethrough.

In another example, as shown in FIG. 4, the stent graft 2, carried at the proximal end 60 of a delivery device, may be pre-loaded with an in-dwelling catheter 70 having a curved configuration. The catheter 70 may extend from the distal external manipulation portion 58 of the delivery device, along the length of the device 56, through the distal end 26 of the side arm or branch 20, through adjacent and attached fenestrations 40 and 48 and curve down in a distal direction though the contralateral stump 14. The catheter 70 may include a guide wire 74 running therethrough. The guide wire 74 may be snared from the contralateral stump 14 from a location inside the lumen of the stump 14 or, alternatively, from a location distal to the distal end 46 of the contralateral stump 14, to create an "up and over pathway" or "through wire", preferably from one groin to the other groin.

Figure 7:
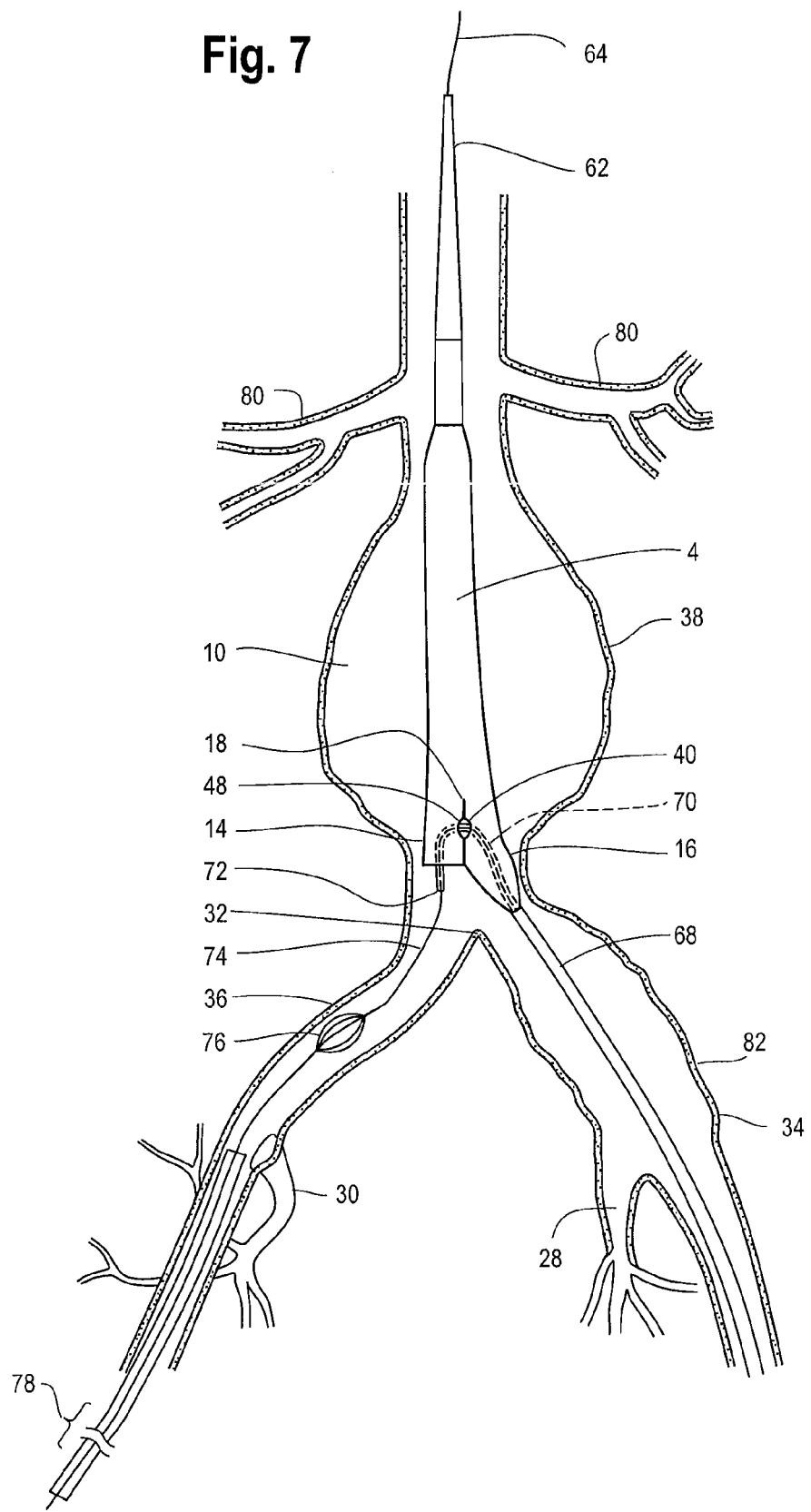

As illustrated in FIG. 6, the delivery device 56 has been extended further in a proximal direction until the graft 2 (still hidden underneath sheath 68) is located in the aorta 10, with the main graft body 4 spanning aneurysm 38 (as illustrated in FIGS. 3 and 4). As shown in FIG. 7, the sheath 68 of one embodiment of the pre-loaded device (illustrated in FIG. 4) has been withdrawn slightly to release the main body 4 of the graft 2. The curved tip 72 of the indwelling catheter 70 and the indwelling guide wire 74 running through the catheter 70 has been extended down the contralateral iliac artery 36. A snare catheter 78 has been deployed into the contralateral common iliac artery 36 and a snare 76 of the snare catheter 78 has been extended to grasp the guide wire 74. The guide wire 74 is extracted via the snare catheter 78 so that it becomes an "up and over" through-wire as shown in FIG. 7. Examples of the use of an indwelling catheter with a curved tip to facilitate snaring from a contralateral iliac artery is taught in U.S. patent application Ser. No. 11/600,655 entitled 'Stent Graft Introducer' and Ser. No. 11/788,285 entitled 'Twin Bifurcated Stent Graft', the teachings of which are incorporated herein in their entireties.

Figure 8:
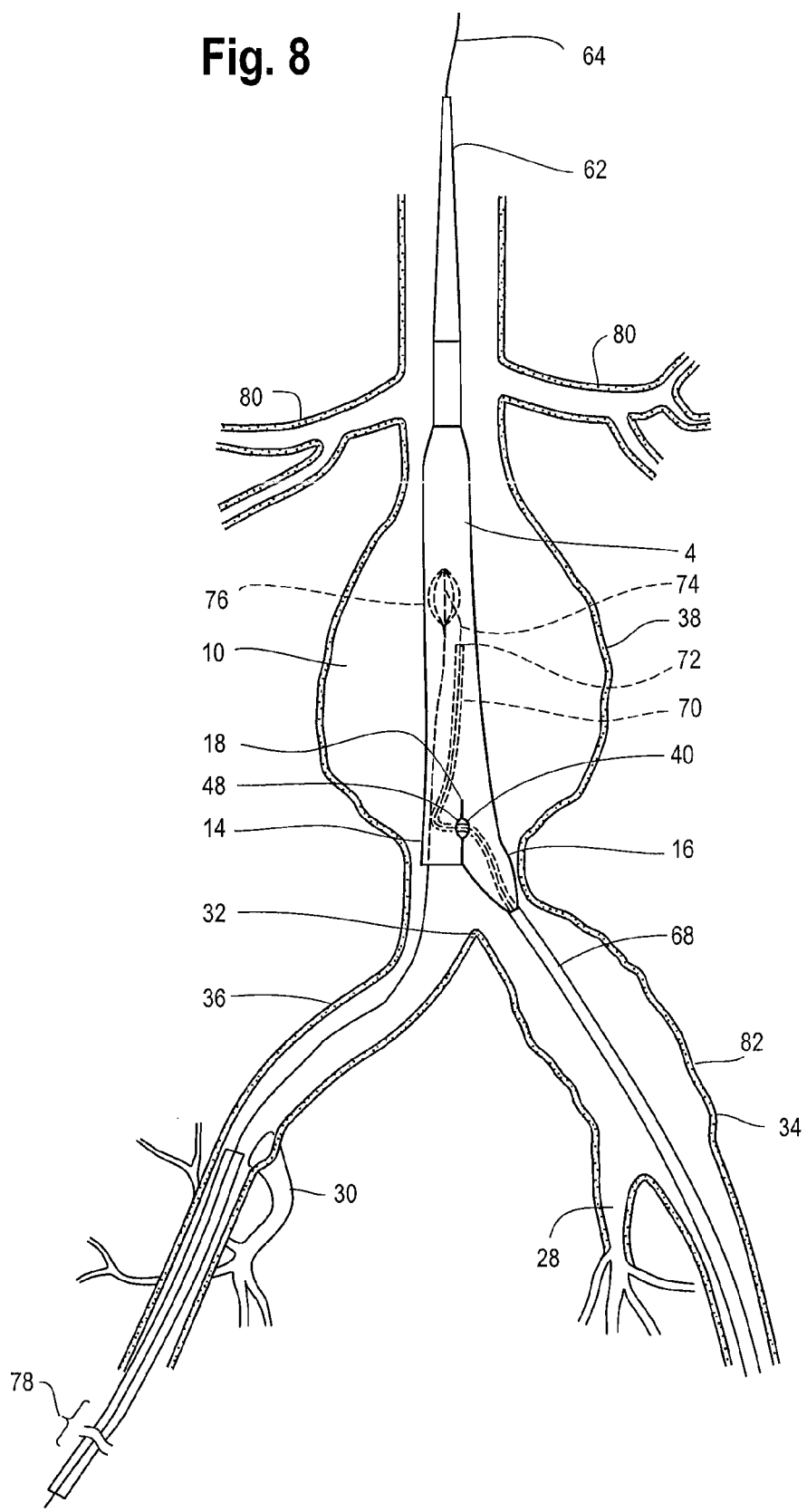

Placement of a though-wire using the pre-loaded stent graft 2 as illustrated in FIG. 3 (which may be carried on delivery device 56) may be similar to that described above with respect to the embodiment of FIG. 4. In particular, the device 56 may be deployed over a guide wire 64 as shown in FIGS. 5 and 6 (where the graft is still covered by sheath 68) until the nose cone 62 is located proximal to the aneurysm 38. As shown in FIG. 8, the sheath 68 may be partially withdrawn, such that the stump 14 and main graft body 4 are uncovered and the main graft body can be seen spanning aneurysm 38 (as also illustrated in FIG. 3) and the graft bifurcation 18 is substantially adjacent to the aortic bifurcation 32. However, in this example, the pre-loaded catheter 70 preferably does not include a curved tip. Rather, the tip 72 of the catheter 70 is preferably substantially straight (although may be flexible) and terminates at a location in the lumen 6 of the main graft body 4. A snare catheter 78 may be deployed into the contralateral iliac artery 36 and a snare 76 of the snare catheter 78 extended to grasp the guide wire 74. The guide wire 74 may then be extracted via the snare catheter 78 so that it becomes a through-wire extending from one groin, over the aortic bifurcation 32, to the other groin.

In addition to the above described examples and embodiments, it is also contemplated that the through-wire may be placed in the vasculature by various other acceptable methods and techniques, and introduced through various locations to establish the "up and over" pathway.

With the pathway established by any one or more of the above-mentioned methods and techniques, additional exemplary steps of delivering and deploying the stent graft 2 will be described. For example, as shown in FIGS. 5-14 there is schematically illustrated a series of vessels within the human body, including the aorta 10, renal arteries 80 and an aortic bifurcation 32. Extending from the aortic bifurcation 32 are common iliac arteries 34 (ipsilateral) and 36 (contralateral) and the respective internal iliac arteries 28 (ipsilateral) and 30 (contralateral). The systems and methods described herein find particular application in the delivery, placement and deployment of one or more stent grafts therein, although as discussed earlier, the disclosed systems and methods are not restricted to this particular purpose and may be used in a variety of applications as will be appreciated by one of skill in the art. In most cases, the internal iliac arteries 28, 30 cannot be practically accessed from their distal ends remote from the junction with the common iliac artery 34, 36. For illustrative purposes, iliac artery 34 is shown as having a diseased portion, including an aneurysm 82, although, it will be appreciated that one or both common iliac arteries 34, 36 and/or one or both internal iliac arteries 28, 30 may also include diseased portions that may be treated in accordance with the systems and methods described herein.

Figure 9:
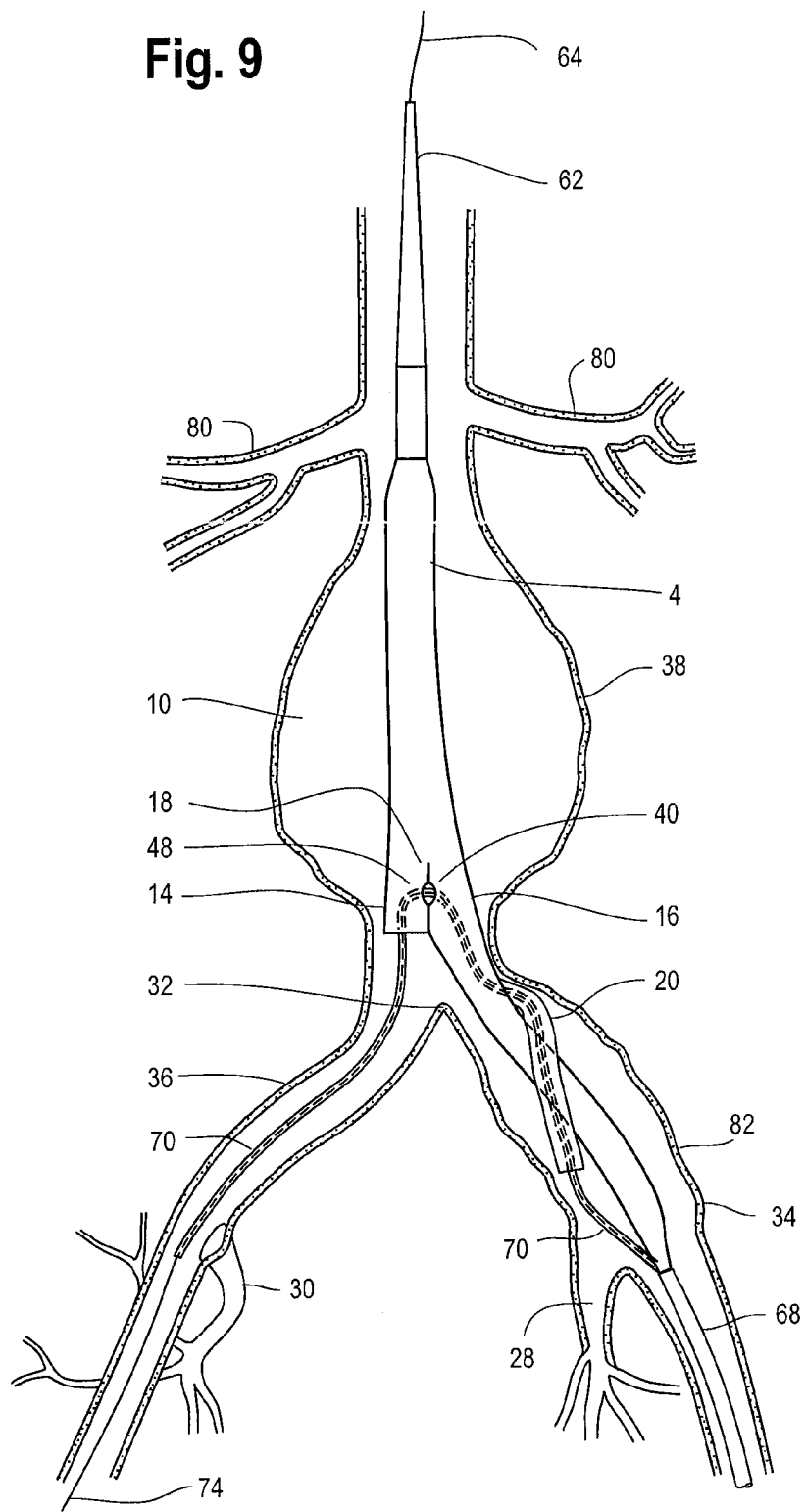

Whether the guide wire 74 is snared inside the main graft lumen 6 (FIGS. 3 and 8) or snared at a location within or adjacent to the lumen of the contralateral stump 14 (FIGS. 4 and 7) as described above, with the graft 2 located so that the main graft body 4 is located in the aorta 10 (and spanning aneurysm 38, if present), the sheath 68 is further withdrawn so that the contralateral stump 14, the side branch 20 and substantially all of the longer leg 16 is uncovered and released from the sheath 68 (except for the distal end of the long leg 16 which is still retained by sheath 68). This stage is shown in FIG. 9. The indwelling catheter 70 is then preferably withdrawn down (distally) into the contralateral iliac artery 36 for removal from the patient's vasculature (such as through a femoral incision, not shown).

Figure 10:
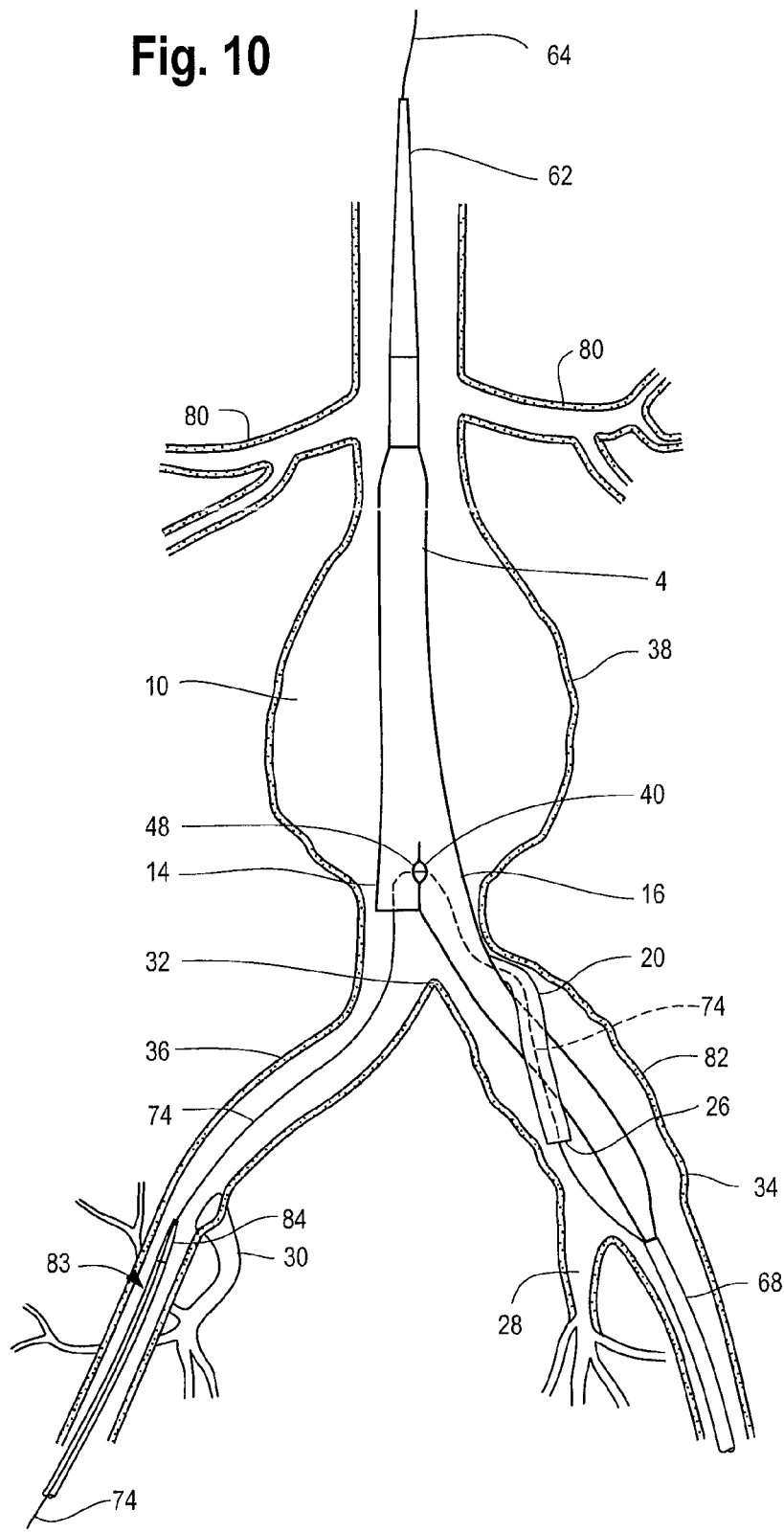
Figure 11:
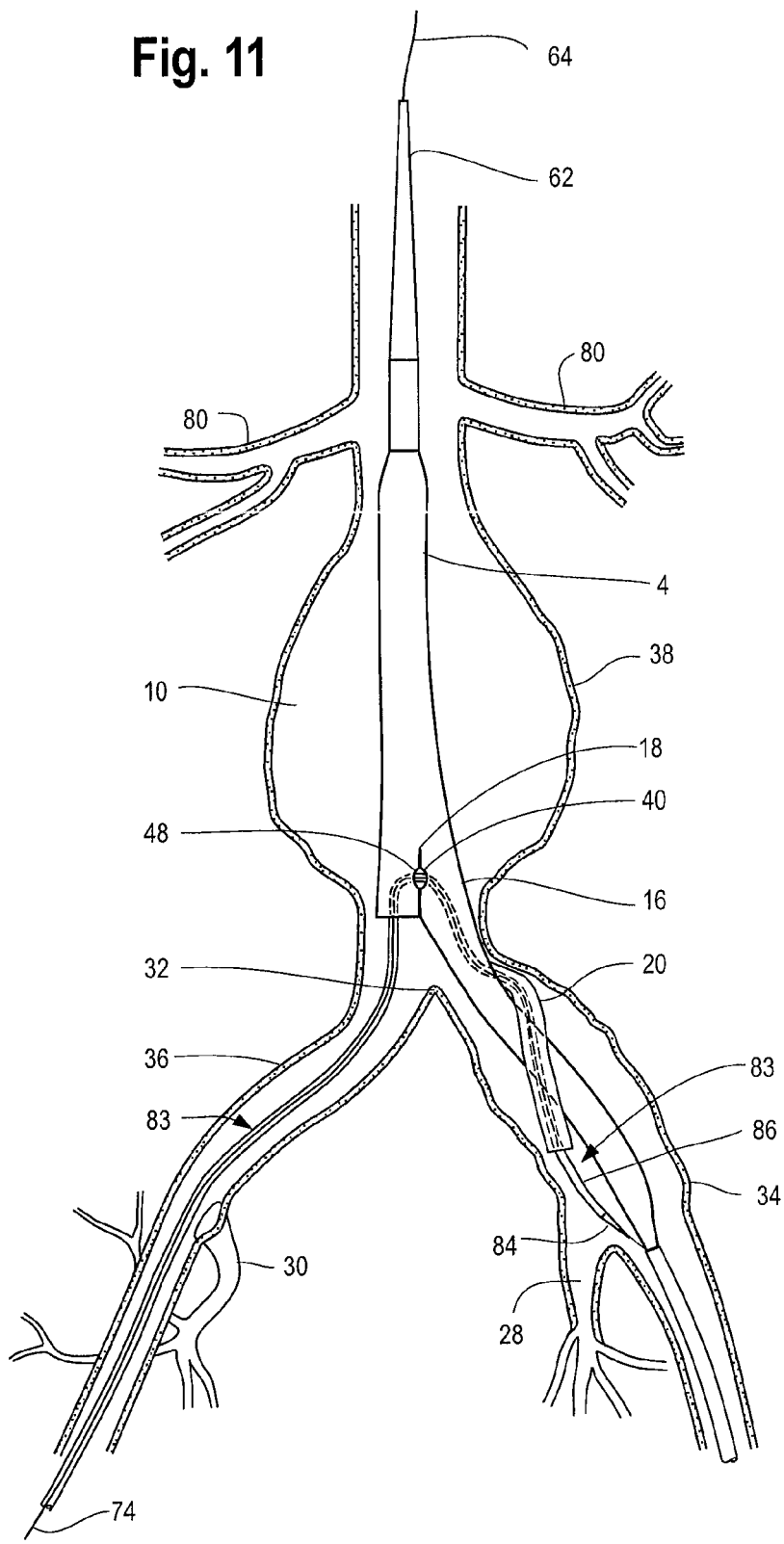
Figure 12:
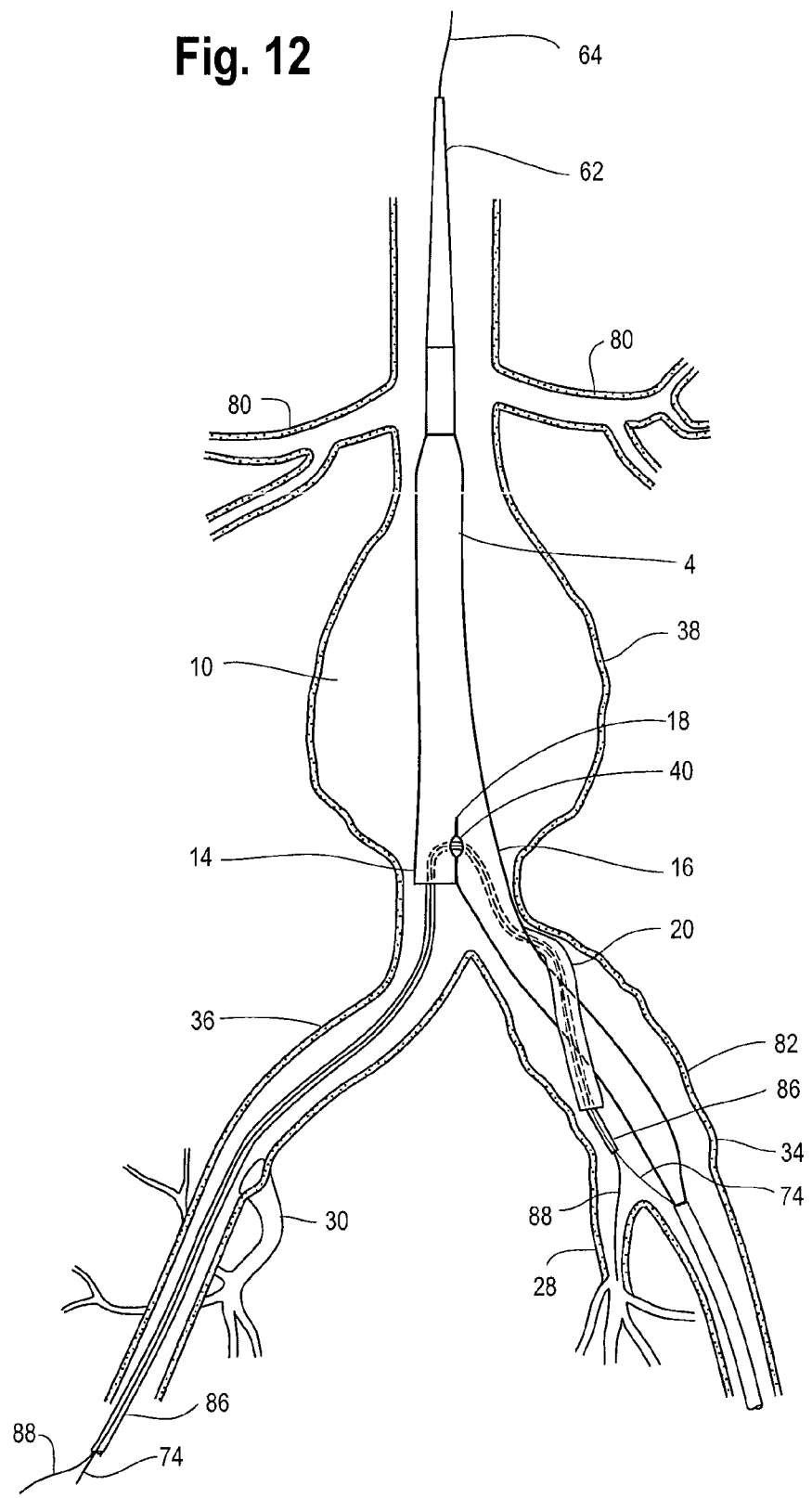

As shown in FIG. 10, a second delivery device 83 including a nose cone dilator 84 and sheath 86 (which covers an extension graft thereunder) is advanced over the guide wire 74 in the contralateral iliac artery 36. The second delivery device 83 is further tracked over the guide wire 74 so that the nose cone 84 of the device 83 extends into the side branch 20 until it exits the distal end of the side branch 20 as shown in FIG. 11. As illustrated in FIG. 12, the second delivery device 83 is then withdrawn leaving the sheath 86 in place. At this stage the indwelling guide wire 74 is still in an up-and-over position. Another guide wire 88 is introduced through the sheath 86 and extended into the internal iliac artery 28.

Figure 13:
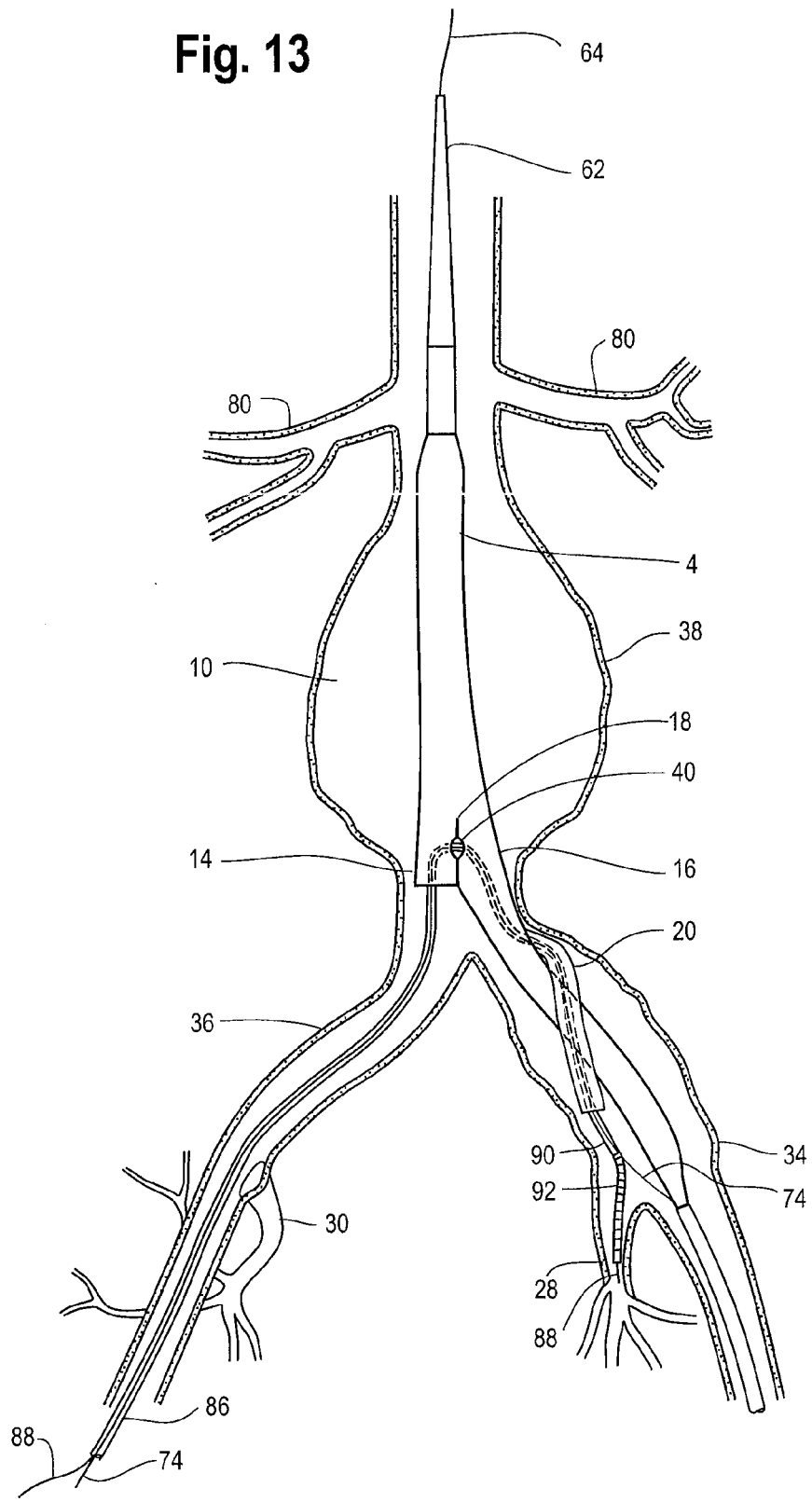

As shown in FIG. 13, a deployment device 90 is deployed over the guide wire 88 into the internal iliac artery 28 so that an expandable covered stent-graft 92 extends into the internal iliac artery 28 from the side arm 20.

In one example, the stent-graft(s) 2, 92 and/or 94 may be a "self-expanding" such that it expands primarily based on its own expansive force without the need for further mechanical expansion. More particularly, a stent made of a shape-memory alloy such as Nitinol may allow the stent graft(s) 2, 92, 94 to return to a predetermined expanded configuration upon removal of a sheath (e.g., 68 and/or 90) or other mechanism that maintains the graft in its compressed, pre-deployment configuration. In another example, stents made of materials such as stainless steel may expand on their own accord once released from constraints holding them in their compressed state. Alternatively, a stent graft 2, 92 and/or 94 may require further manipulation, mechanical or manual expansion, such as by balloon expansion by the user.

Figure 14:
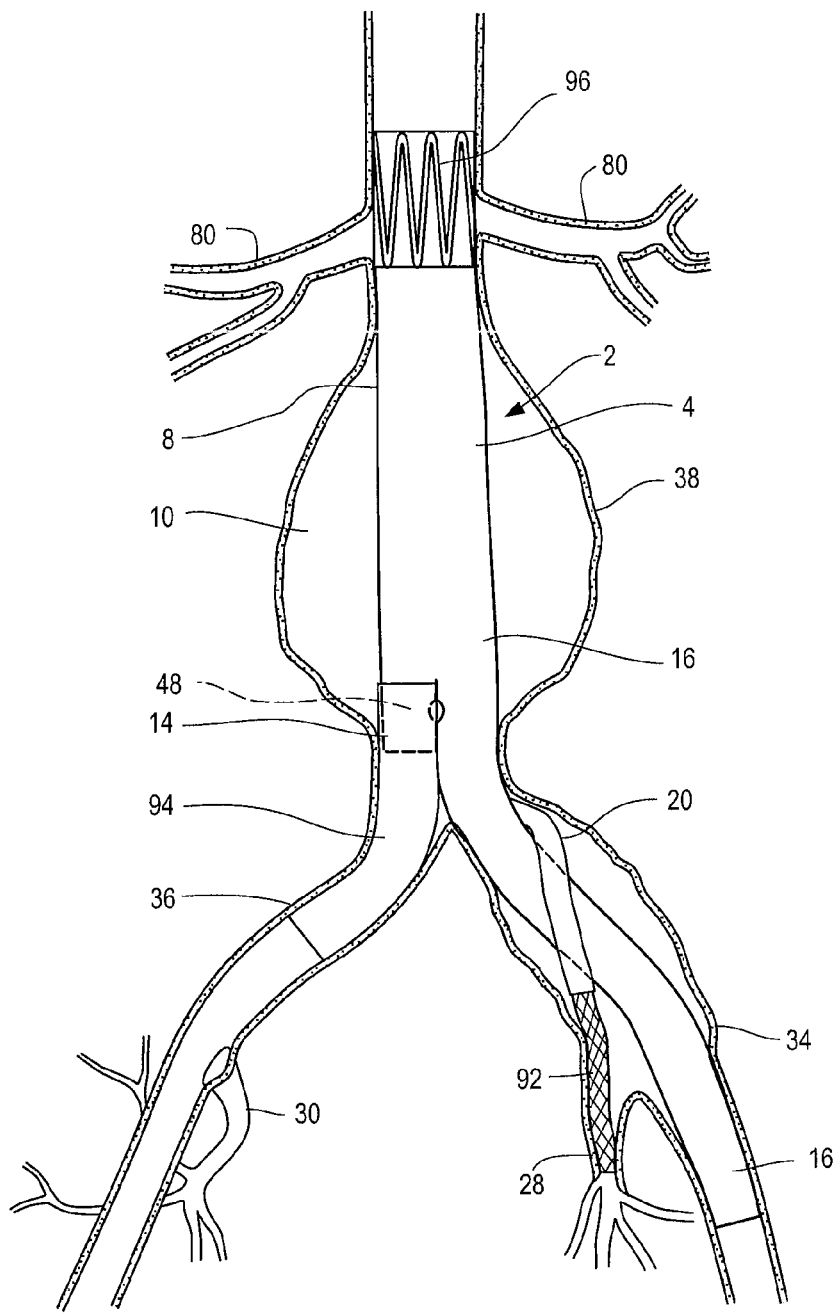

As shown in FIG. 14, the guide wire 74 and/or 88 are then removed and the position of the distal end of the longer leg 16 is set into the iliac artery 34 and the sheath 90 withdrawn, allowing stent 92 to be expanded in the internal iliac artery 28. As shown in FIG. 14, a leg extension graft 94 is then also preferably placed onto the contralateral stump 14, which extends into the iliac artery 36. As mentioned above, placement of the leg extension graft 94 also covers and closes fenestration 48. The proximal end 8 of the main stent graft 2 is released from the delivery device 56 such that a portion of the graft seals into a non-aneurysed portion of the aorta 10. An uncovered suprarenal stent 96 may extend over the renal arteries to provide secure fixation, if desired. Following graft deployment, the delivery device 56 can also be withdrawn from the patient's body.

Such fully deployed stent grafts 2, 92 and 94 are illustrated in exemplary FIG. 14. It can be seen that the bifurcated stent graft 2 as described herein, having adjacent fenestrations 40, 48 formed in inside surfaces of the graft legs 14, 16 and a side branch 20 located relatively more proximally allows precise placement of the "up and over" pathway provided by catheter 70 and guide wire 74 (and subsequent placement of further delivery devices and stent-grafts into the internal iliac artery 28) while also permitting the side branch 20 to properly align with the opening of the branch vessel (such as the internal iliac artery 28) all while keeping the graft bifurcation 18 seated near the aortic bifurcation 32 in patients having a shorter than average iliac arteries.

Throughout this specification, unless the context requires otherwise, the words "comprise" and "include" and variations such as "comprising" and "including" will be understood to imply the inclusion of an item or group of items, but not the exclusion of any other item or group items.

While various examples of the invention have been described, it will be apparent to those of ordinary skill in the art that many more examples and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. An endovascular stent graft comprising:
   a. a main tubular body of a biocompatible graft material having a proximal end portion and a distal end portion and a lumen extending between the proximal and distal end portions;
   b. a first leg defining a first lumen and a second leg defining a second lumen, the first and second legs extending from the distal end portion of the main tubular body and wherein the first and second lumens are in fluid communication with the lumen of the main tubular body; the first and second legs each having facing surface wherein the respective surfaces of the first and second legs are in at least partial abutting relationship;
   c. a first fenestration formed in the surfaces of each of the first and second legs, and wherein the respective first fenestrations at least partially align with each other;

d. wherein at least one of the first and second legs comprises a side branch extending from the at least one of the first and second legs, the side branch comprising a tubular body of a biocompatible graft material having a proximal end portion and a distal end portion and a lumen extending between the proximal and distal end portions, the side branch lumen being in fluid communication with the lumen of the at least one of the first and second legs from which it extends;

e. wherein the proximal end portion of the side branch extends from the at least one of the first and second legs at a location that is substantially adjacent to the first fenestration in the leg from which it extends; and f. wherein the stent graft is configured to be deployed into the vasculature of a patient with at least one of the first and second legs being located in the common iliac artery and the side branch being directed towards an internal iliac artery of the common iliac artery.

2. The graft of claim 1 wherein one of the first and second legs is a longer leg and one is a shorter leg.

3. The graft of claim 2 wherein the side branch extends from the longer leg.

4. The graft of claim 3 wherein each of the first and second legs comprises a distal end portion and wherein at least a portion of the proximal end of the side branch extends from the longer leg at a location that is proximal to the distal end portion of the shorter leg.

5. The graft of claim 2 wherein the side branch extends from the longer leg at a location that is substantially diametrically opposite to the first fenestration in the longer leg.

6. The graft of claim 2 further comprising a second fenestration formed in the longer leg and wherein the proximal end portion of the side branch extends from the second fenestration.

7. The graft of claim 2 wherein the shorter leg further comprises a first stent located proximal to the first fenestration in the shorter leg and a second stent located distal to the first fenestration in the shorter leg.

8. The graft of claim 1 wherein the at least one of the first and second legs further comprises at least one self-expanding stent located proximal to the first fenestration or distal to the first fenestration.

9. The graft of claim 1 wherein the respective first fenestrations are attached.

10. A method for treating a diseased vessel, the method comprising:
  a. introducing a delivery device carrying an endovascular graft into a patient's vasculature, the endovascular graft comprising:
    i. a main tubular body of a biocompatible graft material having a proximal end portion and a distal end portion;
    ii. a long leg and a short leg each extending from the distal end portion of the main tubular body and wherein each of the legs has a surface wherein the respective surfaces of the legs are adjacent and in at least partial abutting relationship;
    iii. a first fenestration formed in each of the surfaces of the long and short legs which fenestrations at least partially align with each other;
    iv. a side branch extending from the long leg, the side branch comprising a tubular body of a biocompatible graft material having a proximal end portion and a distal end portion and a lumen extending therebetween, and wherein the proximal end portion of the side branch extends from the long leg at a location that is substantially adjacent to the first fenestration formed therein;
  b. positioning the endovascular graft in the patient's vasculature such that at least the long leg is located in the common iliac artery and the side branch is directed towards an internal iliac artery of the common iliac artery;
  c. at least partially deploying the endovascular graft in the patient's vasculature.

11. The method of claim 10 further comprising:
  a. introducing a second delivery device though a lumen of the short leg, the second delivery device carrying a second endovascular graft thereon, the second endovascular graft comprising a tubular body defining a lumen;
  b. advancing the second delivery device through the respective first fenestrations formed in the surfaces of the long and short legs and into the lumen of the side branch,
  c. positioning the second endovascular graft within the internal iliac artery;
  d. at least partially deploying the second endovascular graft in the internal iliac artery.

12. The method of claim 10 wherein the respective first fenestrations are attached.

13. An endovascular stent graft comprising:
  a. a main tubular body of a biocompatible graft material having a proximal end portion and a distal end portion and a lumen extending between the proximal and distal end portions;
  b. a first leg defining a first lumen and a second leg defining a second lumen, the first and second legs extending from the distal end portion of the main tubular body to form a bifurcation, wherein the first and second lumens are in fluid communication with the lumen of the main tubular body; the first and second legs each having a surface wherein the respective surfaces of the first and second legs face each other and are in at least partial abutting relationship;
  c. a first fenestration through the first leg surface and a second fenestration through the second leg surface, wherein the first and second fenestrations are at least partially aligned with each other and in fluid communication with each other;
  d. wherein at least one of the first and second legs comprises a side branch extending from the at least one of the first and second legs, the side branch comprising a tubular body of a biocompatible graft material having a proximal end portion and a distal end portion and a lumen extending between the proximal and distal end portions, the side branch lumen being in fluid communication with the lumen of the at least one of the first and second legs from which it extends;
  e. wherein the proximal end portion of the side branch extends from the at least one of the first and second legs at a location that is substantially proximate to the bifurcation.

14. The endovascular stent graft of claim 13, wherein the first leg is a longer leg and the second leg is a shorter leg and the side branch extends from the longer leg.

15. An endovascular stent graft comprising:
  a main tubular body of a biocompatible graft material having a proximal end portion and a distal end portion and a lumen extending between the proximal and distal end portions;
  a first leg defining a first lumen and a second leg defining a second lumen, the first and second legs extending from the distal end portion of the main tubular body and wherein the first and second lumens are in fluid communication with the lumen of the main tubular body; the first and second legs each having a surface wherein the respective surfaces of the first and second legs are in at least partial abutting relationship; and a first fenestration formed in the surfaces of each of the first and second legs, wherein the respective first fenestrations at least partially align with each other.

16. An endovascular stent graft comprising:

a main tubular body of a biocompatible graft material having a proximal end portion and a distal end portion and a lumen extending between the proximal and distal end portions;

a first leg defining a first lumen and a second leg defining a second lumen, the first and second legs extending from the distal end portion of the main tubular body to form a bifurcation, wherein the first and second lumens are in fluid communication with the lumen of the main tubular body; the first and second legs each having a surface wherein the respective surfaces of the first and second legs face each other and are in at least partial abutting relationship;

a first fenestration through the first leg surface and a second fenestration through the second leg surface, wherein the first and second fenestrations are at least partially aligned with each other and in fluid communication with each other.

17. A method for treating a diseased vessel, the method comprising:

introducing a delivery device carrying an endovascular graft into a patient's vasculature, the endovascular graft comprising:

a main tubular body of a biocompatible graft material having a proximal end portion and a distal end portion;

a long leg and a short leg each extending from the distal end portion of the main tubular body and wherein each of the legs has a surface wherein the respective surfaces of the legs are adjacent and in at least partial abutting relationship;

a first fenestration formed in each of the surfaces of the long and short legs which fenestrations at least partially align with each other;

positioning the endovascular graft in the patient's vasculature such that at least the long leg is located in the common iliac artery; and at least partially deploying the endovascular graft in the patient's vasculature.

* * * * *